(12) United States Patent
Adams

(10) Patent No.: US 10,213,285 B1
(45) Date of Patent: *Feb. 26, 2019

(54) INFLATABLE HERNIA PATCH

(71) Applicant: Jason P. Adams, Farmington, NM (US)

(72) Inventor: Jason P. Adams, Farmington, NM (US)

( * ) Notice: Subject to any disclaimer, the term of this patent is extended or adjusted under 35 U.S.C. 154(b) by 131 days.

This patent is subject to a terminal disclaimer.

(21) Appl. No.: 15/265,244

(22) Filed: Sep. 14, 2016

Related U.S. Application Data

(60) Division of application No. 14/795,046, filed on Jul. 9, 2015, now Pat. No. 9,456,887, which is a division of application No. 13/612,034, filed on Sep. 12, 2012, now Pat. No. 9,095,408, which is a continuation of application No. 13/207,281, filed on Aug. 10, 2011, now Pat. No. 8,317,872, which is a continuation of application No. 12/478,482, filed on Jun. 4, 2009, now Pat. No. 8,002,844, which is a continuation of application No. 11/519,652, filed on Sep. 12, 2006, now Pat. No. 7,544,213.

(51) Int. Cl.
*A61F 2/00* (2006.01)

(52) U.S. Cl.
CPC .......... *A61F 2/0063* (2013.01); *A61F 2/0077* (2013.01); *A61F 2002/009* (2013.01); *A61F 2002/0068* (2013.01); *A61F 2210/0004* (2013.01); *A61F 2250/0003* (2013.01)

(58) Field of Classification Search
CPC ............ A61F 2/0063; A61F 2002/0068; A61F 2250/0003; A61F 2250/003; A61F 2210/0004
See application file for complete search history.

(56) References Cited

U.S. PATENT DOCUMENTS

| | | | | | |
|---|---|---|---|---|---|
| 1,213,005 | A | * | 1/1917 | Pillsbury | A61B 17/42 128/836 |
| 3,512,528 | A | * | 5/1970 | Skora | A61F 13/2051 128/836 |
| 3,863,639 | A | * | 2/1975 | Kleaveland | A61B 17/0293 128/850 |
| 4,312,353 | A | * | 1/1982 | Shahbabian | A61M 29/02 128/898 |

(Continued)

OTHER PUBLICATIONS

Davol Inc., "Bard CuraSoft Patch Technique Guide," Product pamphlet, 2003, pp. 1-12.

(Continued)

*Primary Examiner* — Phong Son H Dang
(74) *Attorney, Agent, or Firm* — Pate Baird, PLLC

(57) ABSTRACT

A patch for repairing an intra-abdominal defect is disclosed in one embodiment of the present invention as including a mesh layer providing a grid of material perforated by apertures through the mesh. This mesh is used to reinforce an area around an intra-abdominal defect. A containment layer is secured proximate an edge of the mesh layer. A filler is distributed across the apertures of the mesh to contain a fluid from passing through the mesh. The mesh layer, containment layer, and filler are connected to form a chamber to selectively expand upon receipt of a quantity of fluid between the containment layer and the filler.

14 Claims, 18 Drawing Sheets

(56) References Cited

U.S. PATENT DOCUMENTS

| | | | |
|---|---|---|---|
| 4,452,245 A * | 6/1984 | Usher | A61B 17/04 606/151 |
| 4,693,720 A * | 9/1987 | Scharnberg | A61F 2/0063 427/2.24 |
| 4,823,815 A * | 4/1989 | Watson | A61B 90/02 128/897 |
| 5,176,692 A * | 1/1993 | Wilk | A61B 17/0057 604/103 |
| 5,304,187 A | 4/1994 | Green et al. | |
| 5,309,896 A * | 5/1994 | Moll | A61B 17/00234 128/898 |
| 5,361,752 A * | 11/1994 | Moll | A61B 17/0218 600/205 |
| 5,366,460 A * | 11/1994 | Eberbach | A61B 17/0057 128/887 |
| 5,368,602 A | 11/1994 | De la Torre | |
| 5,370,685 A * | 12/1994 | Stevens | A61B 17/320758 606/167 |
| 5,383,477 A | 1/1995 | DeMatteis | |
| 5,496,345 A * | 3/1996 | Kieturakis | A61B 17/0218 600/204 |
| 5,766,246 A * | 6/1998 | Mulhauser | A61F 2/0063 606/151 |
| 5,769,864 A * | 6/1998 | Kugel | A61F 2/0063 602/44 |
| 5,824,081 A * | 10/1998 | Knapp | A61F 2/12 623/23.72 |
| 6,007,575 A * | 12/1999 | Samuels | A61F 2/01 623/1.15 |
| 6,080,168 A | 6/2000 | Levin et al. | |
| 6,171,318 B1 * | 1/2001 | Kugel | A61F 2/0063 602/44 |
| 6,174,320 B1 * | 1/2001 | Kugel | A61F 2/0063 606/151 |
| 6,224,616 B1 * | 5/2001 | Kugel | A61F 2/0063 128/898 |
| 6,241,768 B1 * | 6/2001 | Agarwal | A61F 2/0063 606/151 |
| 6,280,453 B1 * | 8/2001 | Kugel | A61F 2/0063 602/44 |
| 6,312,462 B1 * | 11/2001 | McDermott | A61F 2/07 623/1.25 |
| 6,575,988 B2 | 6/2003 | Rousseau | |
| 6,599,323 B2 * | 7/2003 | Melican | A61F 2/0045 424/426 |
| 7,001,405 B2 * | 2/2006 | Kieturakis | A61B 17/0218 600/207 |
| 7,404,819 B1 * | 7/2008 | Darios | A61F 2/0063 606/151 |
| 8,920,370 B2 * | 12/2014 | Sholev | A61F 2/0063 604/103 |
| 2002/0147457 A1 * | 10/2002 | Rousseau | A61B 17/0057 606/157 |
| 2003/0078602 A1 * | 4/2003 | Rousseau | A61F 2/0063 606/151 |
| 2004/0019360 A1 * | 1/2004 | Farnsworth | A61F 2/0063 606/151 |
| 2004/0030407 A1 * | 2/2004 | Ketharanathan | A61L 2/0035 623/23.72 |
| 2004/0073257 A1 * | 4/2004 | Spitz | A61B 17/068 606/220 |
| 2004/0172048 A1 * | 9/2004 | Browning | A61F 2/0063 606/151 |
| 2005/0159777 A1 | 7/2005 | Spitz | |
| 2005/0288706 A1 * | 12/2005 | Widomski | A61B 17/0057 606/213 |
| 2006/0025785 A1 * | 2/2006 | Cully | A61F 2/0063 606/151 |
| 2006/0064175 A1 * | 3/2006 | Pelissier | A61F 2/0063 623/23.72 |
| 2006/0116696 A1 * | 6/2006 | Odermatt | A61F 2/0063 606/151 |
| 2006/0240064 A9 * | 10/2006 | Hunter | A61B 17/11 424/423 |
| 2007/0078477 A1 * | 4/2007 | Heneveld, Sr. | A61B 17/0218 606/191 |
| 2007/0142847 A1 * | 6/2007 | Xu | A61L 27/3604 606/151 |
| 2007/0265710 A1 * | 11/2007 | Brown | A61F 2/0063 623/23.72 |
| 2007/0299538 A1 * | 12/2007 | Roeber | A61F 2/0063 623/23.72 |
| 2010/0137999 A1 * | 6/2010 | Shohat | A61B 17/00234 623/23.75 |
| 2013/0231526 A1 * | 9/2013 | Felix | A61B 17/00234 600/37 |

OTHER PUBLICATIONS

Davol Inc., "Bard Kugel Hernia Patch Technique Guide," Product pamphlet, 2000, pp. 1-16.

Davol Inc., "Bard Composix Kugel Patch Technique Guide," Product pamphlet, 2005, pp. 1-52.

Davol Inc., "Bard Ventralex Hernia Patch Technique Guide," Product pamphlet, 2003, pp. 1-16.

Davol Inc., "Bard Modified Kugel Patch Technique Guide," Product pamphlet, 2003, pp. 1-16.

Davol Inc., "Modified Bard PerFix Plug Hernia Repair: Preparational Underlay Patch Technique," Product pamphlet, 2001 pp. 1-2.

Davol Inc., "Laparoscopic Inguinal Hernioplasty: Utilizing Bard 3DMax Mesh," Product pamphlet, 2002, pp. 1-7.

Davol Inc., "Laparoscopic Ventral Herniorrhaphy Utilizing Bard Composix E/X Mesh," Product pamphlet, 2002, pp. 1-23.

U.S. Food and Drug Administration, "Class 1 Recall: Bard Composix Kugel Mesh Patch—Updated," http://www.fda.gov/cdrh/recalls/recall-122205.html, Apr. 20, 2006, pp. 1-2.

* cited by examiner

INFLATABLE HERNIA PATCH

RELATED APPLICATIONS

This application: is a divisional of U.S. patent application Ser. No. 14/795,046; filed Jul. 9, 2015; which is a divisional of U.S. patent application Ser. No. 13/612,034; filed Sep. 12, 2012, and issued as U.S. Pat. No. 9,095,408, on Aug. 4, 2015; which is a continuation of U.S. patent application Ser. No. 13/207,281, filed Aug. 10, 2011, and issued as U.S. Pat. No. 8,317,872, on Nov. 27, 2012; which is a continuation of U.S. patent application Ser. No. 12/478,482, filed Jun. 4, 2009, and issued as U.S. Pat. No. 8,002,844, on Aug. 23, 2011; which is a continuation of U.S. patent application Ser. No. 11/519,652, filed Sep. 12, 2006, and issued as U.S. Pat. No. 7,544,213, on Jun. 9, 2009; all of which are incorporated herein by reference in their entirety.

BACKGROUND

The Field of the Invention

This invention relates to hernia repair and more particularly to apparatus and methods for expanding and maintaining the shape of hernia patches during hernia repair.

The Background Art

With more than 20 million hernia repairs occurring worldwide on an annual basis, hernia repair is the most frequently performed surgical operation in the world. Although there are many different techniques for repairing hernias, these techniques generally can be classified as either tension or tension-free repairs.

For many years, tension repair was the primary procedure used to treat people with hernias. Using this techniques, an incision is generally made in the abdomen over the hernia site. Any protruding tissue is pushed back into the correct position within the abdominal cavity and the hernial defect is mended with stitches or sutures. Because the stitches or sutures generally exert tension on the sides of the defect in order to keep it closed, this technique may cause more pain and discomfort than other repair techniques and there is typically a higher probability that the hernia will recur. Consequently, this technique is generally only suitable for very small hernias.

Tension-free repair techniques are currently the most common techniques and generally utilize a piece of mesh to bridge the hernial defect. These meshes are typically constructed of synthetic materials, such as Goretex®, Teflon®, Dacron®, Marlex®, Prolene®, or the like. Tension-free repairs may be performed using either open surgery or laparoscopic techniques. In open surgery, a surgeon usually makes an incision over the hernial defect and folds and inserts a mesh patch through the incision. This patch may be manually unrolled and positioned inside the abdomen before being fastened with staples, sutures, or the like to the abdominal wall over the defect. Once the mesh is securely attached, tissue grows through the mesh to create a strong but flexible layer that mimics the abdominal wall.

Tension-free mesh repairs may also be performed laparoscopically. Using this technique, a mesh patch is usually folded and inserted into the abdomen through a small incision away from the hernial defect. The patch is then moved to the region of the hernia, unfolded, positioned over the defect, and attached to the abdominal wall. This surgery is generally referred to as posterior hernia repair because the hernia is repaired from behind the abdominal wall.

One challenge in performing both open surgery and laparoscopic mesh repairs is unfolding and positioning a mesh patch inside the abdomen once inserted. Because there is typically very little room to work and visibility may be limited inside the abdomen, it is often difficult or awkward to unroll and position a mesh patch prior to attachment. This may result in a patch that is undesirably creased or poorly positioned, creating unwanted tension or discomfort within the abdomen. As a result, some manufacturers of mesh patches have integrated devices, such as "memory recoil rings" into their patches to allow them to spring open and lie flat once positioned inside the abdomen. These recoil rings are flexible enough to be rolled or folded tightly to allow insertion through an incision in the abdomen.

Nevertheless, these recoil rings may also be prone to break under the stress of folding, rolling, or placement inside the intra-abdominal space. In fact, several different models of patches from at least one manufacturer have been recalled due to instances of breakage inside the abdomen. These breaks can cause various problems, such as bowel perforations or chronic intestinal fistulae (i.e., abnormal connections or passageways between the intestines and other organs).

In view of the foregoing, what is needed is a mesh patch that is easily unfolded and positioned within the abdomen, while reducing the safety concerns associated with patches using recoil rings or other expansion mechanisms. Ideally, an improved expansion mechanism should be incorporated into a mesh patch and left inside the abdomen after closing the incision. Furthermore, such a patch would ideally be useful in both open surgery and laparoscopic procedures.

BRIEF SUMMARY OF THE INVENTION

In view of the foregoing, in accordance with the invention as embodied and broadly described herein, a patch for repairing an intra-abdominal defect is disclosed in one embodiment of the invention as including a mesh layer providing a grid of material perforated by apertures therethrough. This mesh is used to reinforce an area around an intra-abdominal defect. A containment layer may be secured proximate an edge of the mesh layer. A filler may be distributed throughout the apertures of the mesh to prevent a fluid from passing through the mesh. Alternatively a layer or filler may form a wall secured to the mesh. The mesh layer, containment layer, and filler are connected at the respective edges thereof to form a chamber between the containment layer and filler to selectively expand upon receipt of a quantity of fluid between the containment layer and the filler.

In certain embodiments, a patch in accordance with the invention may include a fill mechanism connected to introduce a fluid into the chamber. Suitable fill mechanisms may include, for example, a chemical to generate a gas, a syringe, a pneumatic bulb, a source of compressed-gas or liquid such as sterile saline, a pump, or the like. In certain embodiments, the fill mechanism may include a conduit connected to introduce a fluid (e.g. liquid or gas) into the chamber. In other embodiments, a fill mechanism, such as a gas-generating chemical, may be located inside the fluid chamber to produce a fluid from inside the patch.

In selected embodiments, the filler, the containment layer, or both may be formed of a bioabsorbable material that degrades inside the abdomen over time. In selected embodiments, the filler is a bioabsorbable material embedded to seal the apertures of the mesh. The containment layer may, in some embodiments, be formed of the same material as the filler.

In certain embodiments, the patch may include an anti-adhesion layer substantially impervious to cell growth and non-adherent to live tissue. This layer may help to prevent intestines or other internal organs from adhering to and possibly being damaged by the patch. In selected embodiments, the containment layer is also the anti-adhesion layer. In other embodiments, the filler material may provide the anti-adhesion layer. The anti-adhesion layer may be formed of various types of polymers such as polyfluorinated materials.

In certain embodiments, to keep the fluid chamber relatively flat, rigid, and to aid in unfolding the patch, the chamber forms one or more inflatable rings. In other embodiments, the chamber may form one or more inflatable ribs. Similarly, the chamber may include one or more regions of securement connecting the containment layer to the mesh layer. These regions of securement may, in certain embodiments, be provided by fasteners such as a welds, adhesives, stitches, staples, or the like.

In another embodiment in accordance with the invention, a method for repairing an intra-abdominal defect may include providing a patch including a mesh layer integrated with a fluid chamber expandable to extend the mesh layer. The patch may then be folded and inserted through an incision in the abdomen to repair an intra-abdominal defect. The patch may then be unfolded by urging fluid into the fluid chamber, positioned over the intra-abdominal defect, and attached to the abdominal wall to reinforce an area proximate the intra-abdominal defect. The fluid chamber may be left inside the abdomen upon closing the incision.

In certain embodiments, the method further includes deflating the expandable fluid chamber. This may be accomplished, for example, by puncturing the expandable fluid chamber, allowing fluid to slowly leak through apertures in the expandable chamber, cutting a conduit leading to the expandable fluid chamber, allowing fluid to escape through a conduit leading to the expandable chamber, or the like. In certain embodiments, puncturing may include piercing the fluid chamber with a suture member, such as a needle, staple, forceps, or the like.

In selected embodiments, urging fluid into the fluid chamber may include urging fluid through a conduit leading to the fluid chamber. In other embodiments, urging fluid into the fluid chamber includes chemically generating fluid inside the fluid chamber.

In another embodiment in accordance with the invention, a patch for repairing an intra-abdominal defect includes a mesh for attachment to an area proximate an intra-abdominal defect and a fluid chamber integrated into the patch and connected to the mesh. The fluid chamber, upon inflating, extends to maintain the shape of the mesh to facilitate placement and attachment of the mesh proximate the intra-abdominal defect.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the apparatus and methods of the present invention, as represented in the Figures, is not intended to limit the scope of the invention, as claimed, but is merely representative of selected embodiments of apparatus and methods in accordance with the invention. The invention will be best understood by reference to the drawings, wherein like parts are designated by like numerals throughout.

Figure 1:
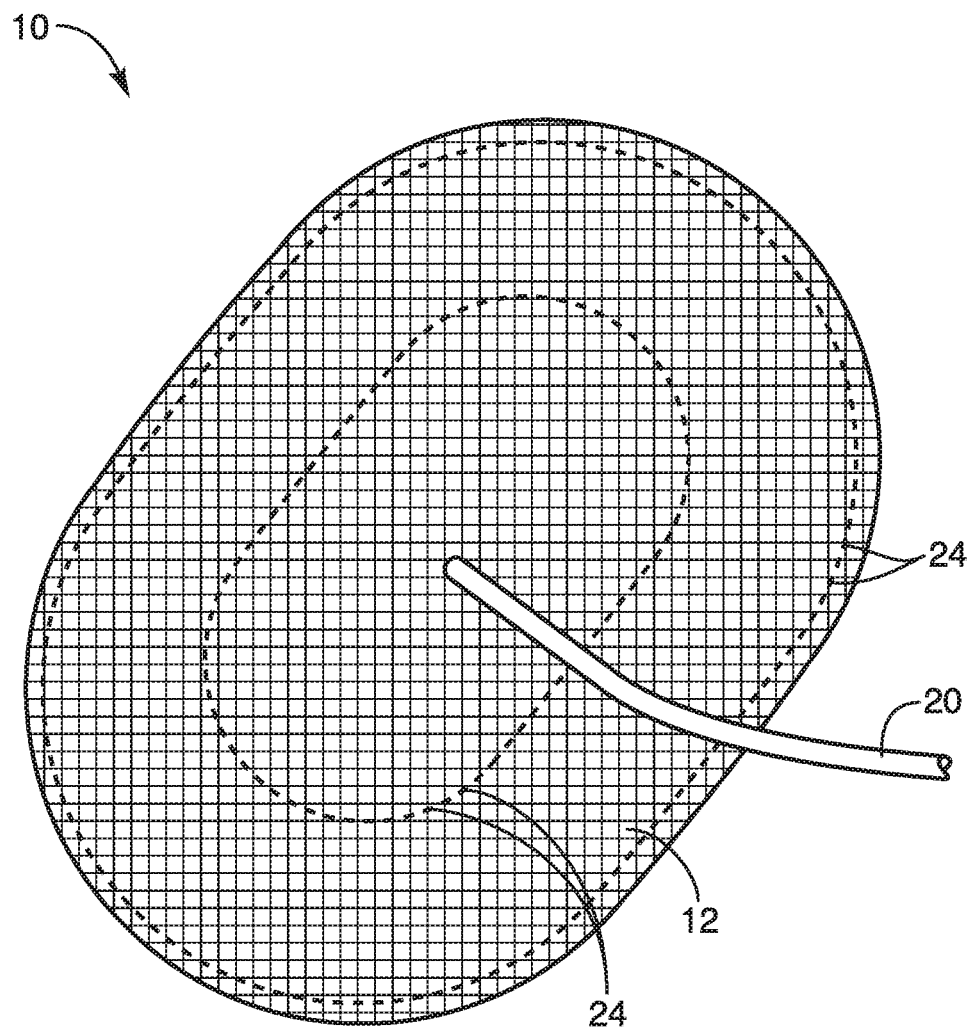
FIG. 1 is a perspective view of one embodiment of an improved hernia patch in accordance with the invention.
Figure 2:
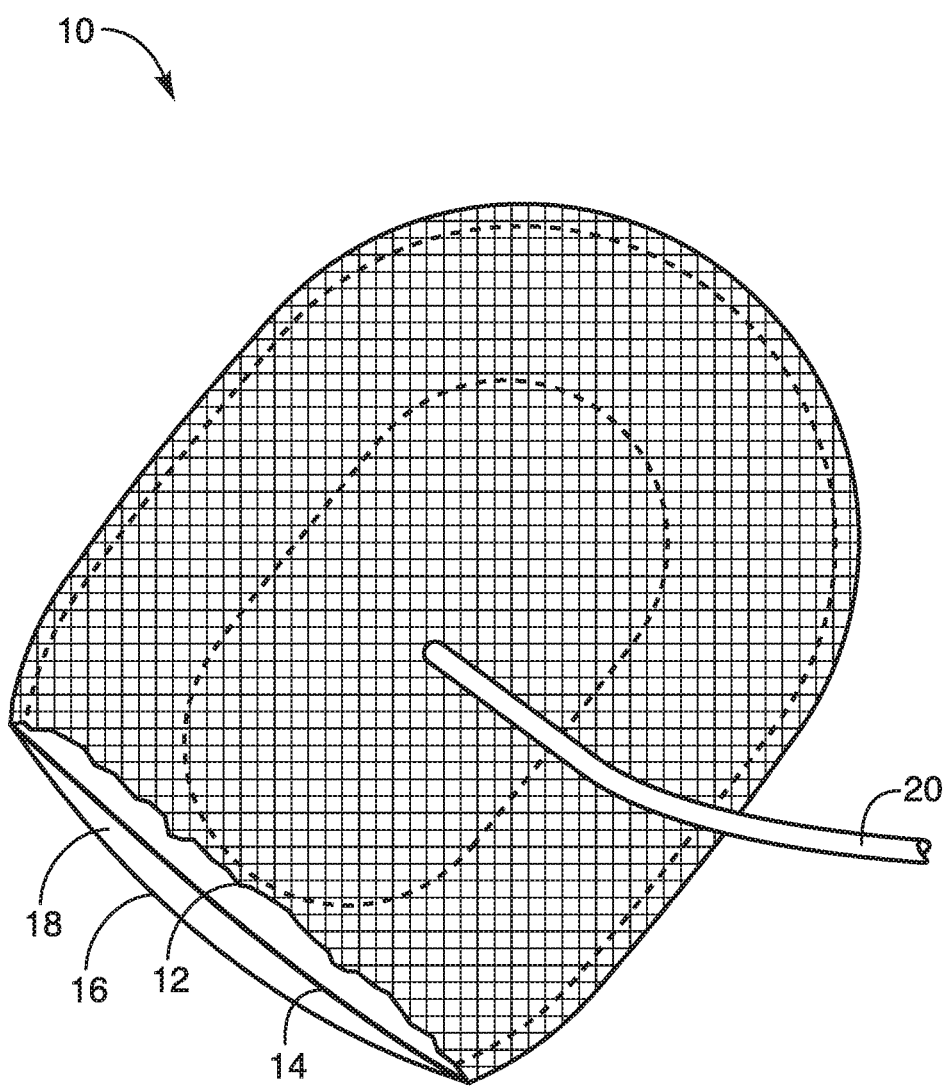
FIG. 2 is a cutaway perspective view of the patch illustrated in FIG. 1.

Referring to FIGS. 1 and 2, in general, a patch 10 in accordance with the invention for repairing a hernia or other intra-abdominal defect may include a mesh layer 12, a filler 14, and a containment layer 16. As explained in more detail hereafter, the mesh layer 12, containment layer 16, and filler 14 may be connected to form a chamber that expands upon receipt of a quantity of fluid between the containment layer 16 and the filler 14.

A mesh layer 12 may generally be formed of a grid of material perforated by apertures configured to receive tissue growth therethrough to reinforce an area around an intra-abdominal defect. The mesh layer 12 may be constructed of any of a wide variety of materials including but not limited to non-fibrous or fibrous, non-porous or porous materials such as Marlex®, Prolene®, Atrium®, Trelex®, Goretex® (ePTFE), Surgical Membrane®, Dualmesh®, Teflon® (PTFE mesh), Mersilene® (braided Dacron® mesh), Surgipro® (braided polypropylene mesh), MaxcroMesh® (perforated PTFE patch), silastic, Vypro®, or the like, to name just a few. The pore size of these meshes may vary greatly and in some cases the pores are sized to allow admission of macrophages, fibroblasts, blood vessels and collagen fibers into the pores. This may reduce the chance of hernia recurrence and provide ingrowth characteristics that mimic normal tissue healing. A mesh 12 may also conform to the abdominal wall musculature anatomy.

A filler 14 may be used to seal the apertures of the mesh layer 12 to prevent fluid from passing through the apertures. A filler 14 may, in certain embodiments, simply be a layer 14 adjacent to, and optionally attached periodically to, the mesh layer 12 to prevent fluid from passing through the mesh 12. In other embodiments, the filler 14 may be integrated into the mesh layer. For example, in certain embodiments, the filler may be a bioabsorbable material used to temporarily seal the apertures of the mesh layer 12. Suitable bioabsorbable materials may include, for example, polylactide polymer, polyglycolic acid, polycaprolactone, gelatin, or the like. After the patch 10 is attached to the abdominal wall, this bioabsorbable material may degrade and be absorbed into the body. This may open and expose the apertures of the mesh 12 to allow body tissue to attach to and intergrow with the mesh layer 12.

As mentioned, a containment layer 16 may be attached to the mesh layer 12 (which is sealed by the filler 14) to form a fluid chamber 18. The containment layer 16 may, in certain embodiments, be attached to the mesh layer 12 along an edge using stitches 24 (as shown), adhesive, staples, welds, or the like. As shown, rows or areas of stitches 24, adhesive, staples, welds, or the like, may be provided at selected locations along the patch to keep the patch 10 relatively flat or planar when inflated.

The chamber 18 formed by the containment layer 16 and mesh layer 12 may be expanded to extend the patch 10 upon receipt of a fluid. This may allow the patch 10 to unfold and lay flat while inside the abdomen to facilitate placement and attachment to the abdominal wall. In certain embodiments, a fluid such as a biocompatible liquid (e.g., water, saline, etc.) or gas (e.g., carbon dioxide) may be urged into the chamber 18 through a conduit 20. This fluid may be urged through the conduit 20 using a fill mechanism such as a gas-generating chemical, a syringe, a pneumatic bulb, a source of compressed-gas, a pump, or the like.

Like the filler 14, the containment layer 16 may also be formed from a bioabsorbable material. This may allow the containment layer 16 to degrade and absorb into the body after the patch 10 has been inflated and attached inside the abdomen. Thus, in certain embodiments, both the filler 14 and containment layer 16 may be formed of a bioabsorbable material, leaving only the mesh layer 12 inside the abdomen after these two layers 14, 16 have dissolved.

In other embodiments, the mesh layer 12 may also be formed of a bioabsorbable material, although it may typically be designed to degrade at a slower rate than the filler 14 or containment layers 16. This may allow time for tissue to attach and intergrow within the mesh 12 before the mesh 12 dissolves. In other embodiments, the containment layer 16 may be formed of an anti-adhesion material, such as Goretex® or other polyfluorinated polymers, to minimize tissue adhesions, such as intestinal or other organ adhesions, to the mesh layer 12 and tissues growing therethrough.

Figure 3:
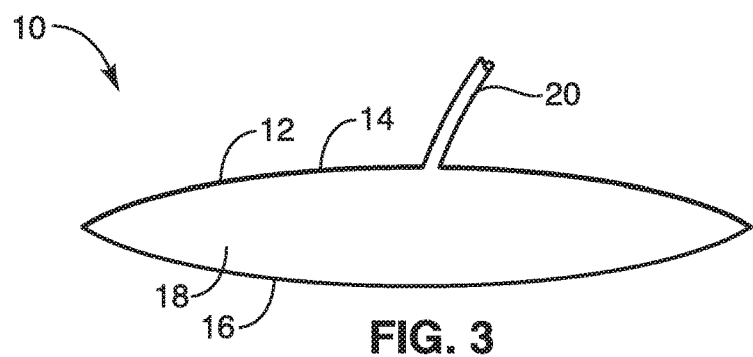
FIG. 3 is a simplified side profile view of one embodiment of a hernia patch in accordance with the invention.

Referring to FIG. 3, in selected embodiments, a patch 10 in accordance with the invention may include a mesh layer 12 and filler 14 integrated into a single layer 12, 14. For example, as mentioned hereinbefore, the filler 14 may simply be a material sealing the apertures of the mesh 12 and possibly the pores of the mesh itself if such exist. A containment layer 16 may be attached to the layer 12, 14, thereby creating a chamber 18. This chamber 18 may be inflated upon receipt of a fluid to expand and unfold the patch 10. This fluid may, in certain embodiments, be received through a conduit 20. This conduit 20 may either attach to the mesh and filler layer 12, 14, as shown, to the containment layer 16, or to both such as when fitted between them. In certain embodiments, the place of attachment of the conduit 20 may differ based on the type of surgery.

For example, for open surgery, the conduit 20 may be attached to the mesh and filler layer 12, 14 because the patch 20 is typically inserted through an open incision immediately above the hernial defect. The conduit 20 may be routed through the open incision to a fill mechanism to urge fluid into the patch 10. In laparoscopic procedures, however, the conduit 20 may be attached to the containment layer 16 because the defect is normally repaired from behind the abdominal wall. Here, the conduit 20 may be routed through a laparoscopic port in the abdomen located some distance away from the hernial defect.

As previously mentioned, the filler 14, containment layer 16, mesh 12, or combinations thereof, may be formed of a bioabsorbable material. In this way, the chamber 18 may degrade and disappear after the patch 10 is inserted and attached to the abdominal wall. In other embodiments, the containment layer 16 may be formed of an anti-adhesion material, such as Goretex® or some other inert polymer.

Figure 4:
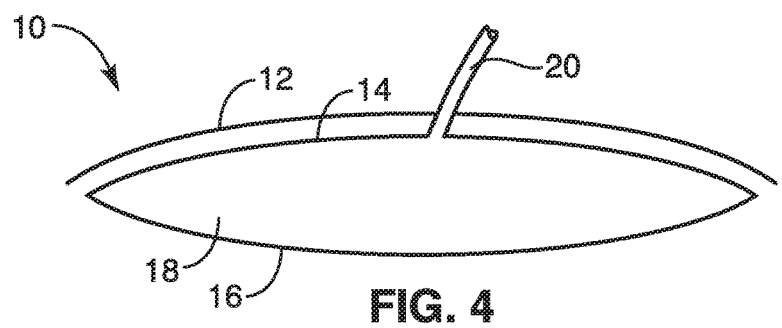
FIG. 4 is a simplified side profile view of another embodiment of a hernia patch in accordance with the invention.

Referring to FIG. 4, in another embodiment, a patch 10 in accordance with the invention may be integrated to include a mesh layer 12 and filler layer 14 as two separate layers only connected periodically such as at points therealong, an edge, or the like. A containment layer 16 may be attached to the filler layer 14 to form a chamber 18. A conduit 20 may supply fluid to the chamber 18. Although embodied as a separate layer, the filler layer 14 may nevertheless prevent fluid from flowing out of the chamber 18 through apertures of the mesh layer 12.

The mesh layer 12 may be attached to the filler layer 14 using stitches, adhesives, staples, welds, or other means of attachment. Furthermore, like the previous example, either the filler layer 14, containment layer 16, or both may be made of a bioabsorbable material. In other embodiments, either the filler layer 14 or containment layer 16 may be formed of an anti-adhesion material, the other layer typically being bioabsorbable. For example, in one embodiment, the containment layer 16 may be formed of an anti-adhesion material. In another embodiment, the filler layer 14 may be formed of an anti-adhesion material, such as Goretex®, and the containment layer 16 may be formed of a bioabsorbable material. When the containment layer 16 degrades and disappears, the filler layer 14 may be exposed to prevent intestines, internal organs, or other tissue form adhering to the mesh layer 12.

Figure 5:
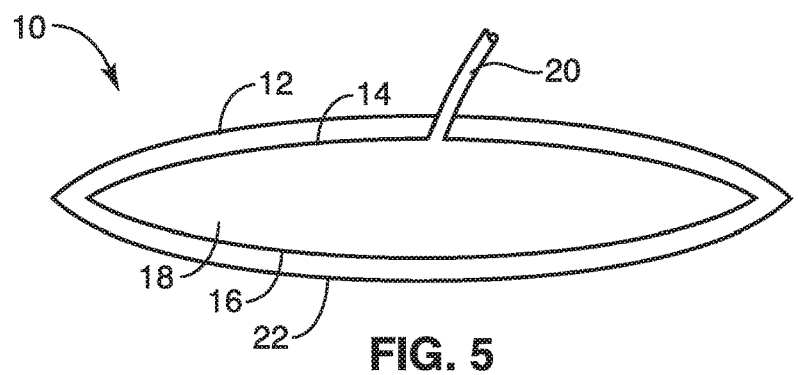
FIG. 5 is a simplified side profile view of another embodiment of a hernia patch in accordance with the invention.

Referring to FIG. 5, in yet another embodiment, a patch 10 in accordance with the invention may include a containment layer 16 and an anti-adhesion layer 22 as separate layers. For example, the patch 10 may include a mesh layer 12 and a filler layer 14 to prevent fluid from passing through the mesh layer 12. The containment layer 16 may be attached to the filler layer 14 or mesh layer 12 to form a chamber 18. A separate anti-adhesion layer 22 may be attached beneath (e.g. inward from) the containment layer 16 to prevent improper adhesions of tissues to the patch 10. In certain embodiments, the filler layer 14 and containment layer 16 may be bioabsorbable such that the chamber 18 degrades and disappears, leaving only the mesh layer 12 and anti-adhesion layer 22 inside the abdomen.

Figure 6:
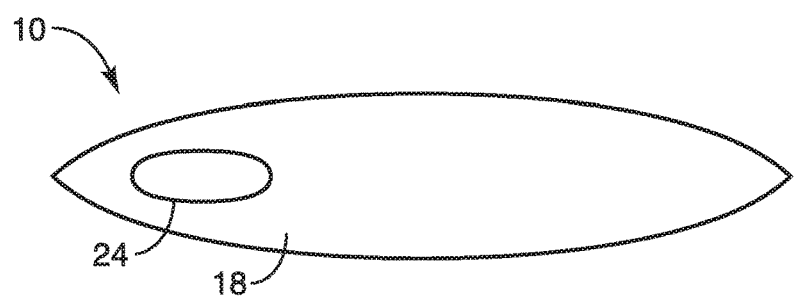
FIG. 6 is a simplified side profile view of another embodiment of a hernia patch in accordance with the invention.

Referring to FIG. 6, in other embodiments, a patch 10 may include a fill mechanism inside the chamber 18. For example, in one contemplated embodiment, a chemical combination may be stored within a container 24 in the chamber 18. This container 24 may be ruptured to expose to one another the chemicals inside the chamber 18. For example, acetic acid and sodium bicarbonate make carbon dioxide and neither the component nor gas is toxic, all of them being bioabsorbable. This or another mechanism may initiate a gas-generating chemical reaction inside the chamber 18 to inflate and extend the patch 10. The generated gas may be biocompatible and may be released from the chamber 18 by puncturing the chamber 18, such as during attachment of the patch 10 to the abdomen.

Figure 7:
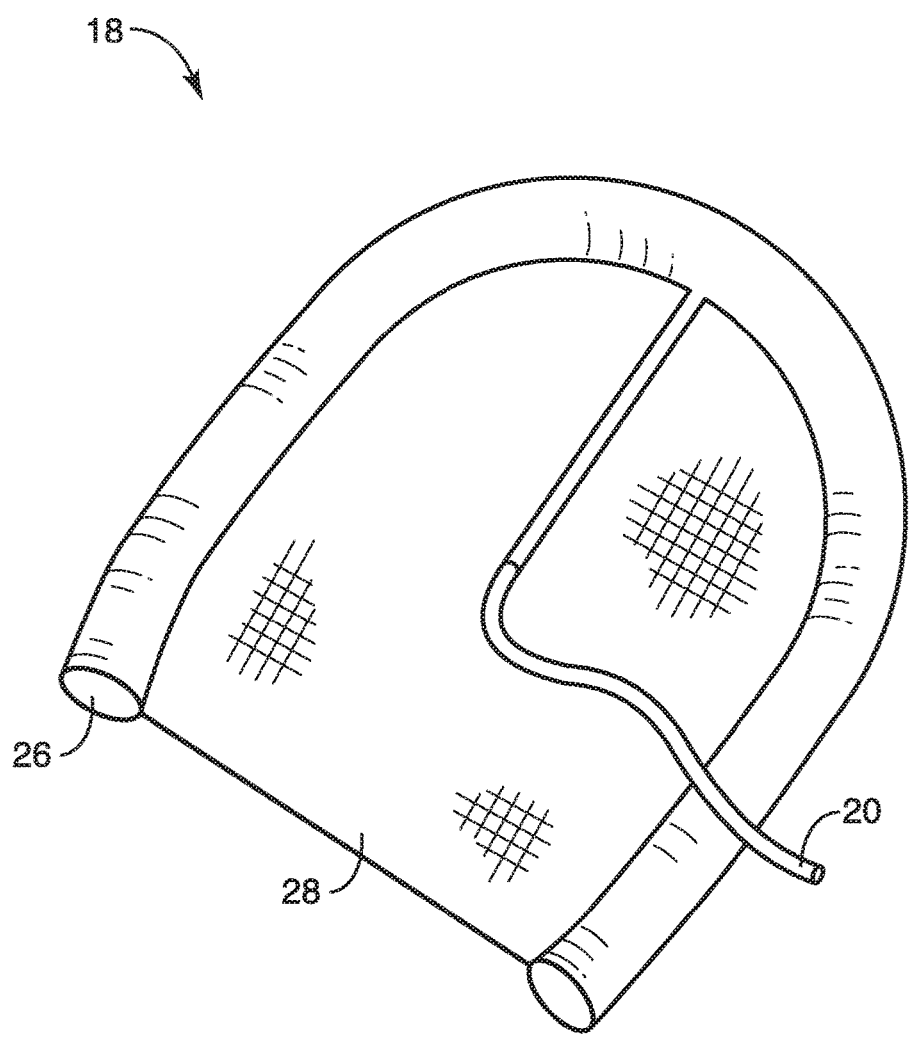
FIG. 7 is a cutaway perspective view of one embodiment of a fluid chamber for incorporation into a patch in accordance with the invention.

Referring to FIG. 7, in selected embodiments, a chamber 18, as described in association with FIGS. 1 through 6, may be designed to urge the patch 20 toward a substantially planar configuration during inflation. That is, a chamber 18 may tend to expand in all directions when inflated. Thus, a chamber 18 may be designed to stay relatively flat, or planar, even when expanded. For example, in one embodiment, the chamber 18 may include an inflatable ring 26 near, just inside, or around the outer edge of the patch 10. This ring 26 may inflate through a conduit 20 or other filling means. When inflated, this ring 26 may expand to extend the patch 10 in a planar orientation to facilitate placement and attachment of the patch 10 to the abdominal wall.

In certain embodiments, a sheet-like portion 28 may span the space inside the ring 26. In selected embodiments, this portion 28 may be useful to attach a patch 10 to the abdominal wall without puncturing the chamber 26. For example, stitches, sutures, staples, or the like, may pierce the inner mesh portion 28 without puncturing the outer chamber 26. This may allow the ring-shaped chamber 26 to maintain the shape of the patch 10 until the patch 10 is adequately positioned and attached to the abdominal wall. Once attached, the chamber 26 may be deflated by puncturing the chamber 26, cutting the conduit 20, tearing off the conduit 20, of by piercing the chamber 26 with a staple, suture, or the like.

Figure 8:
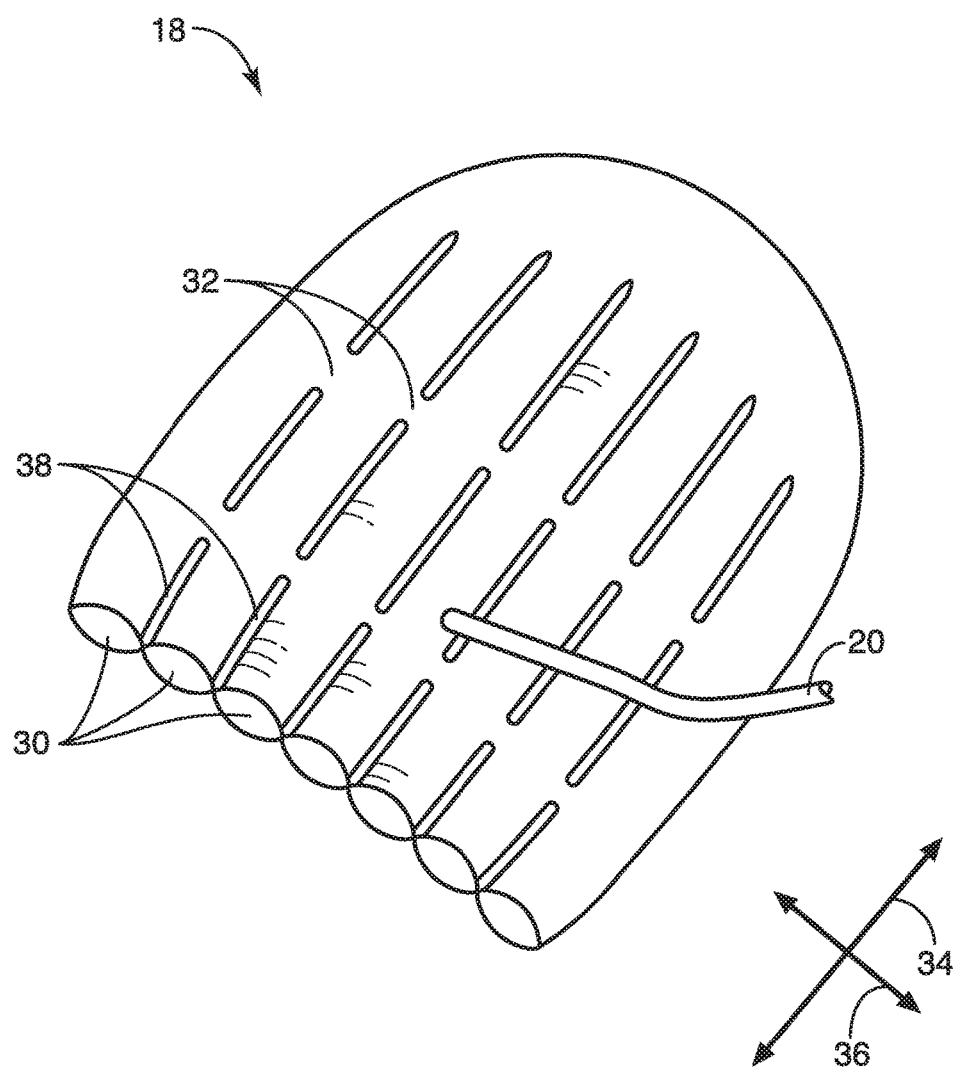
FIG. 8 is a cutaway perspective view of another embodiment of a fluid chamber for incorporation into a patch in accordance with the invention.

Referring to FIG. 8, in other embodiments, a chamber 18 may include one or more inflatable ribs 30 for extending and providing rigidity to the patch 10 primarily in a first direction 34. These ribs 30 may be created by providing one or more linear securement regions 38 along the length 34 of the chamber 18. In selected embodiments, the ribs 30 may be connected by passageways 32. These passageways 32 may provide rigidity primarily in a second direction 36, which may be perpendicular to the first direction 34. Like the previous example, the rib structure may serve to keep the chamber 18 substantially flat and comparatively stiff while a patch 10 is placed and attached to the abdominal wall.

Figure 9:
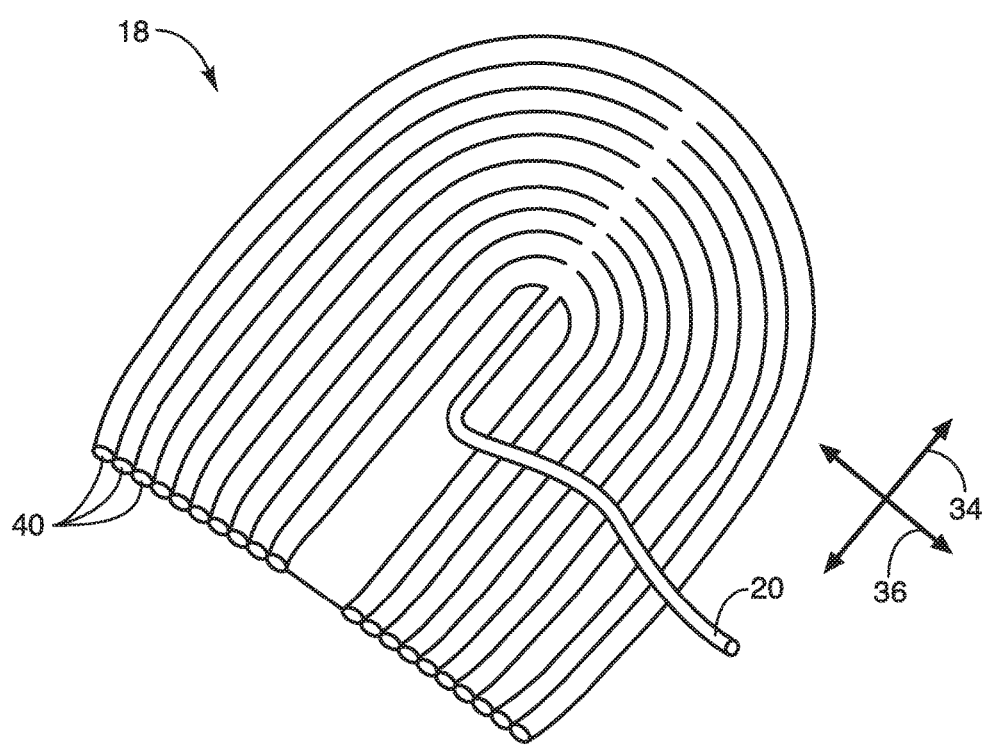
FIG. 9 is a cutaway perspective view of another embodiment of a fluid chamber for incorporation into a patch in accordance with the invention.

Referring to FIG. 9, in yet another embodiment, a chamber 18 may include a plurality of concentric inflatable rings 40. Like the example of FIG. 7, these rings 40 may expand when inflated to extend a patch 10 and facilitate placement and attachment of the patch 10 to the abdominal wall. However, by using multiple rings 40, the rings 40 may be smaller, thereby providing a patch 10 that is thinner and more compact when inflated. Furthermore, the multiple rings 40 may provide rigidity to the patch 10 in multiple directions 34, 36 during placement and attachment of the patch 10 to the abdominal wall.

Figure 10:
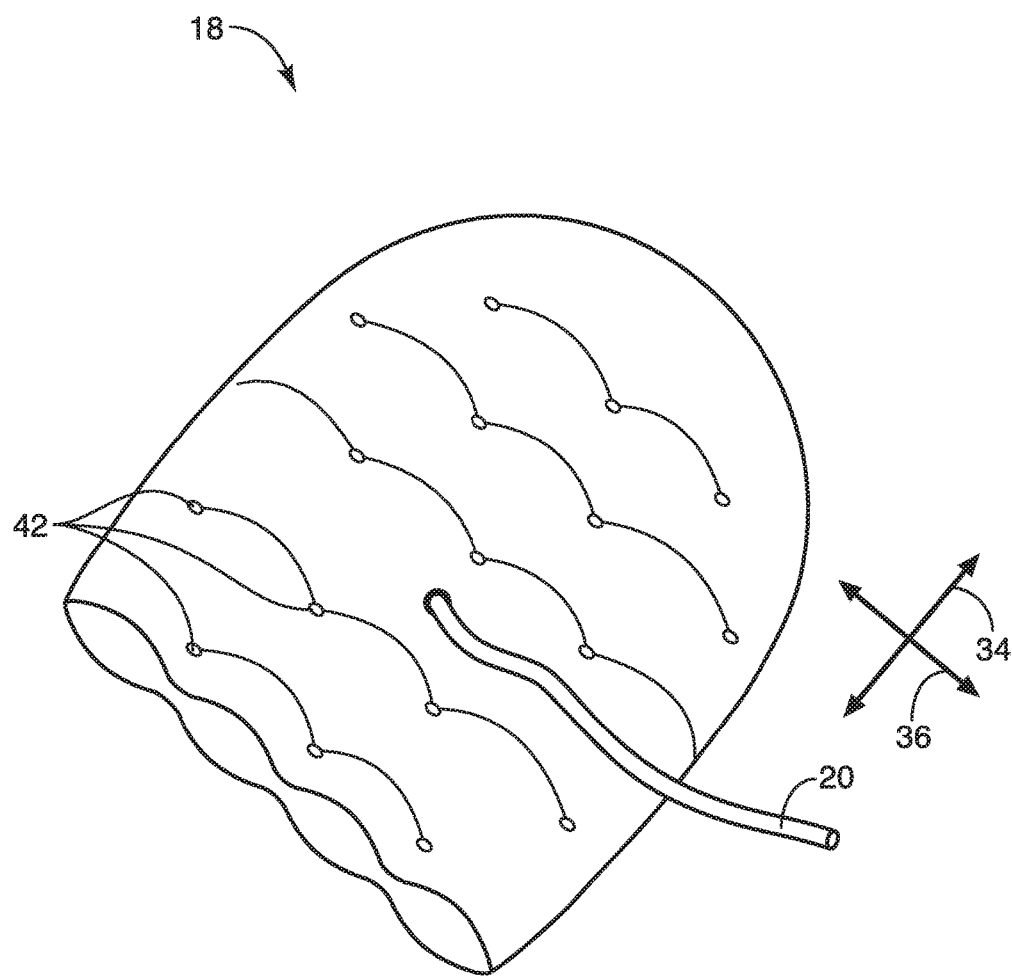
FIG. 10 is a cutaway perspective view of another embodiment of a fluid chamber for incorporation into a patch in accordance with the invention.

Referring to FIG. 10, in another embodiment, the chamber 18 may include one or more small regions 42 of securement, or "kiss-throughs," to keep the chamber 18 relatively thin and flat when inflated. One benefit of this embodiment is that the small regions 42 of securement may provide greater stiffness to the patch 10 in multiple directions 34, 36.

Figure 11:
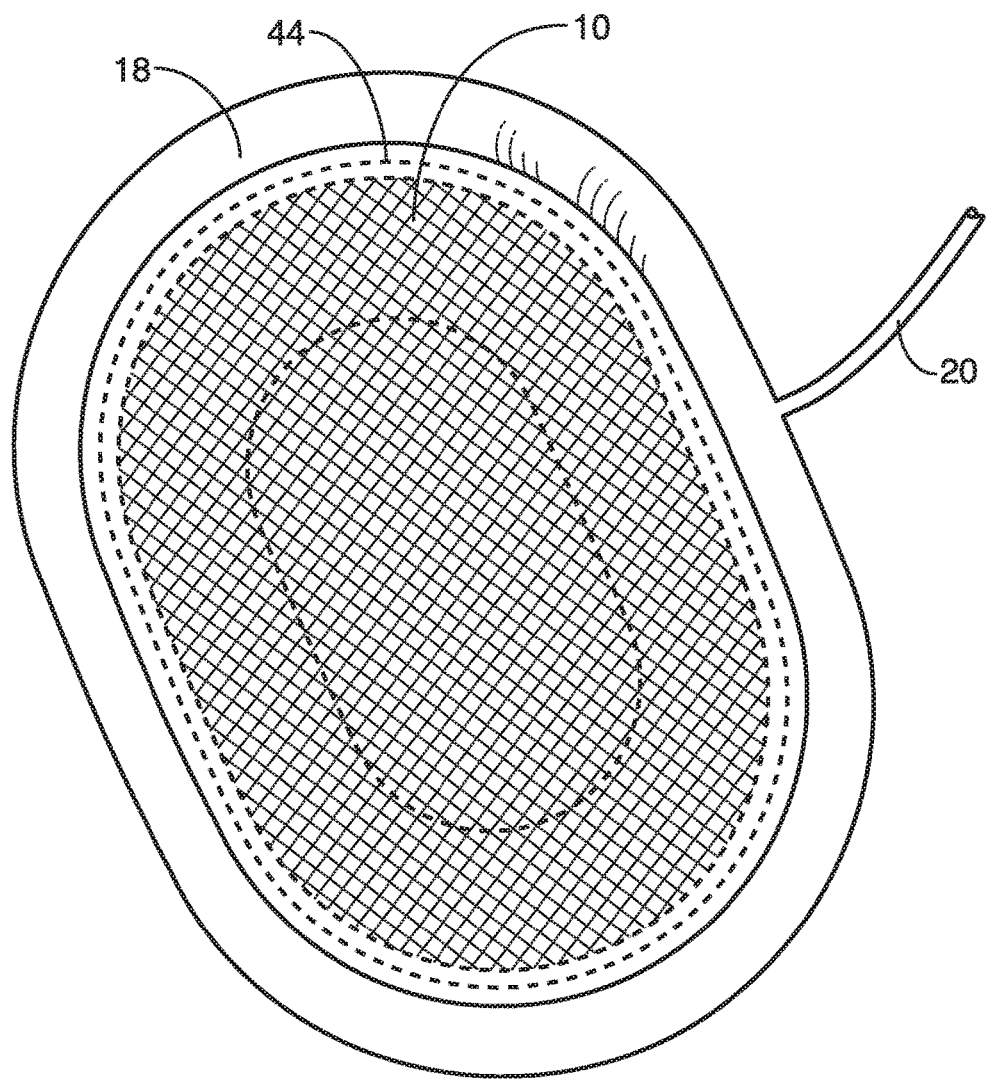
FIG. 11 is a perspective view of one embodiment of a patch having an integrated, yet separable (e.g. tear-away) fluid chamber.
Figure 12:
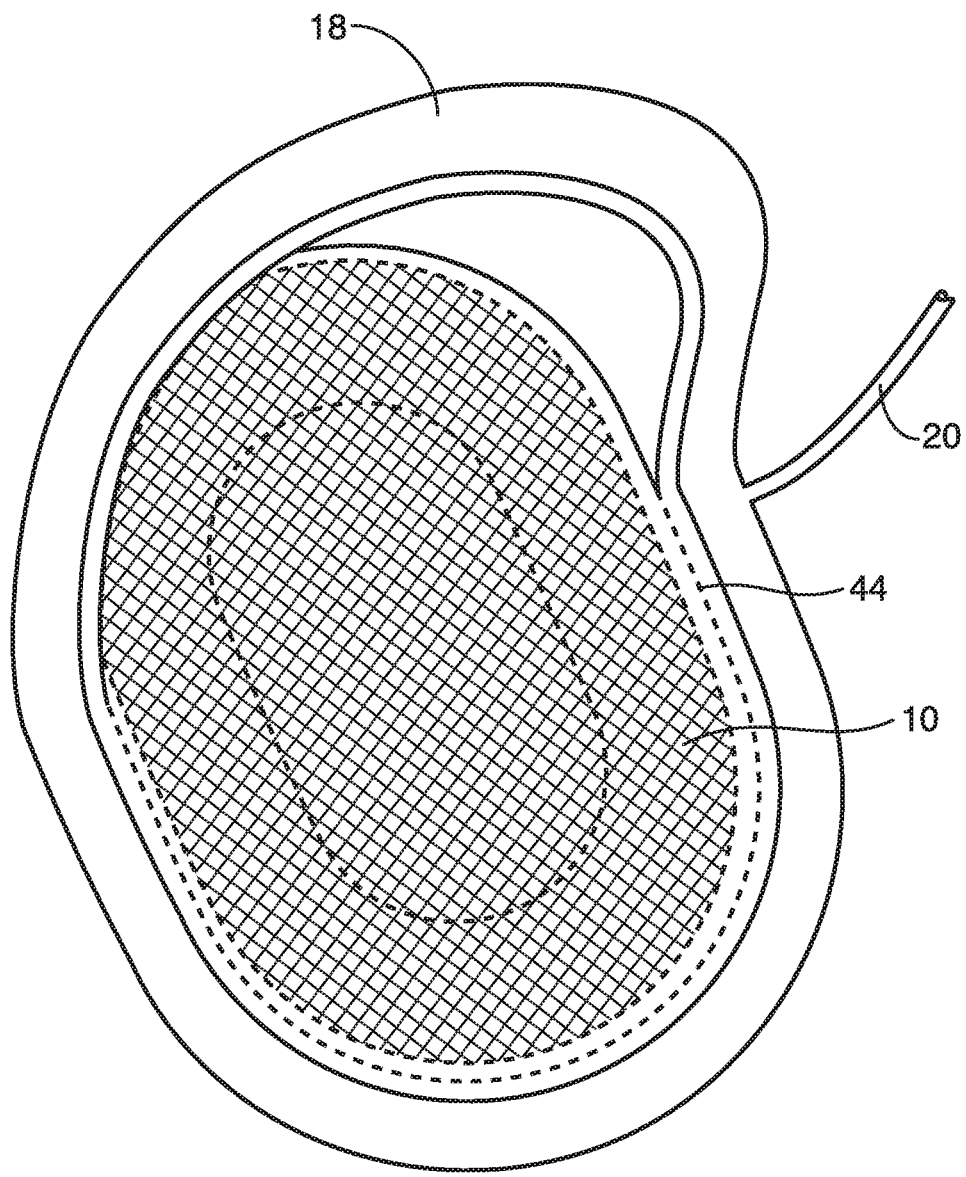
FIG. 12 is another view of the patch illustrated in FIG. 11 showing detachment of the fluid chamber.

Referring to FIGS. 11 and 12, in selected embodiments, a chamber 18 may be detachable from a patch 10 in accordance with the invention after the patch 10 is secured to the abdominal wall. For example, in selected embodiments, a patch 10 may include a chamber 18 detachable from the patch 10 by way of a scored or perforated line 44. To extend the patch 10, the chamber 18 may be inflated through a conduit 20. The patch 10 may then be positioned and attached to the abdominal wall with stapes, sutures, stitches, or the like. Once attached, the chamber 18 may be detached from the patch 10 by tearing it along the score line 44. The chamber 18 may then be removed from the abdomen through an incision, such as through a laparoscopic port. This embodiment may be most suitable for laparoscopic procedures.

Figure 13:
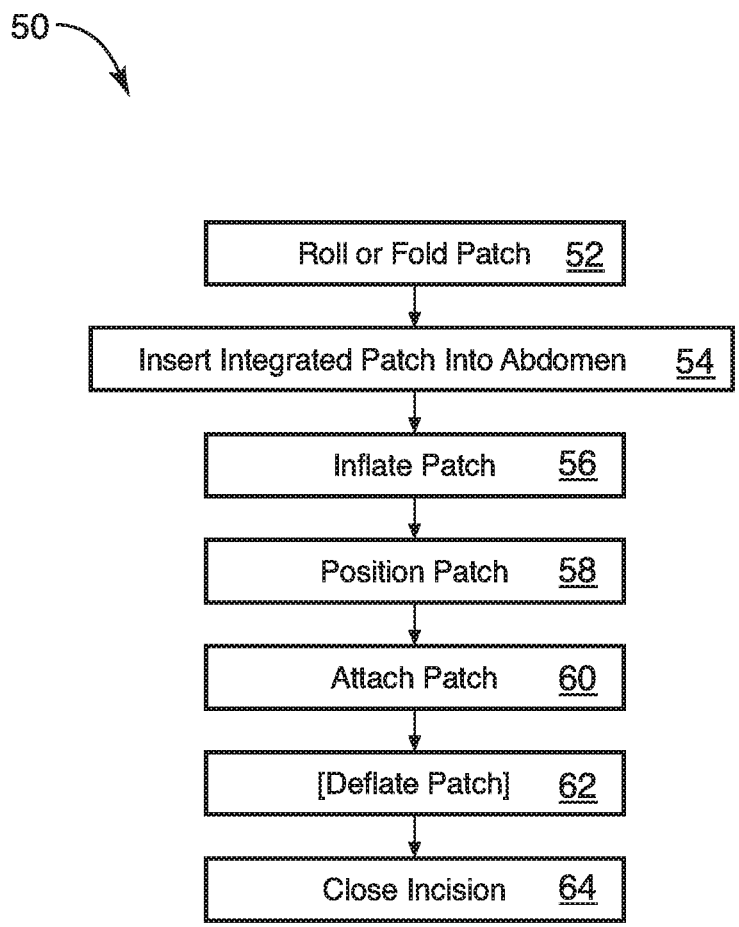
FIG. 13 is a schematic flow chart of one embodiment of a method for repairing a hernia using a patch in accordance with the invention.

Referring to FIG. 13, one embodiment of a method 50 for repairing an intra-abdominal defect may include first, providing a patch 10 comprising a mesh layer 12 integrated with a fluid chamber 18 expandable to extend the mesh 12. The method may then include rolling 52, folding 52, or otherwise compacting 52 the patch 10 and inserting 54 the patch 10 into the abdomen. For the purposes of this description, the terms "compacting," "folding," and "rolling" may be used interchangeably.

In open surgery, this may include, for example, rolling 52 or folding 52 the patch 10 around a finger and inserting the patch 10 into the incision with the finger (e.g., for smaller patches), or simply rolling 52 the patch, such as into thirds, and inserting 54 the patch 10 through the open incision (e.g., for larger patches). For laparoscopic procedures, this may include folding 52 or rolling 52 the patch 10 around a surgical tool, such as a sponge holder or forceps, to insert 54 the patch 10 through a port in the abdomen.

Once inside the abdomen, the patch 10 may then be inflated 56 to unfold and extend the patch 10 to give it a substantially flat orientation. This step may include urging a fluid, such as water, saline, air, carbon dioxide, nitrogen, or the like, into the patch chamber 18. As previously mentioned, this may be accomplished using a fill mechanism such as a syringe, pneumatic bulb, source of compressed-gas, pump, or the like, to urge fluid through a conduit 20 leading to the chamber 18. In other embodiments, this step 56 may be accomplished from inside the patch 10, such as by internally generating a fluid through a chemical reaction.

Once inflated, the patch 10 may be positioned over the hernial or other intra-abdominal defect. In certain embodiments, such as in open surgery procedures, the conduit 20 may be used to center the patch over the hernial defect. That is, because the open incision is generally made over the hernial defect, the conduit 20 (assuming it attaches to a central region of the patch 10) may be used to center the patch 10 over the defect simply by centering the conduit 20 through the incision. In other embodiments, the patch 10 may also be urged against the abdominal wall by gently pulling on the conduit 20 prior to attachment. This may also help the patch 10 to conform to the abdominal wall which may be rounded or curved.

Next, the patch 10 may be attached 60 to the abdominal wall. As previously mentioned, the patch 10 may be attached to the abdominal wall using staples, sutures, or other means of attachment. Once properly attached, the chamber 18 may optionally be deflated 62. This deflation step 62 may include puncturing the fluid chamber 18 (e.g., using a needle, forceps, staple, etc.), cutting the conduit 20 leading to the fluid chamber 18, simply allowing fluid to escape back through the conduit 20 leading to the chamber 18, or actually drawing fluid out of the chamber 18 through the conduit 20.

In certain embodiments, the fluid chamber 18 may be designed to allow fluid to slowly leak through perforations in the chamber 18 after expansion (e.g. filling, inflation). In embodiments where all or part of the chamber 18 is bioabsorbable, the chamber 18 may also deflate once a portion of the chamber 18 has degraded. In certain embodiments, the attachment step 60 may be sufficient to deflate the chamber 18. That is, staples, sutures, or the like used to attach the patch 10 may also puncture and deflate the chamber 18 in a single step.

After the patch 10 has been properly attached and deflated, drained, or otherwise collapsed, cleanup procedures such as cutting or tearing off the conduit 20 may be performed. The incision or incisions (either open or laparoscopic) may then be closed 64. Because the chamber 18 is integrated into the patch 10, the walls of the chamber 18 may be left inside the abdomen.

Figure 14:
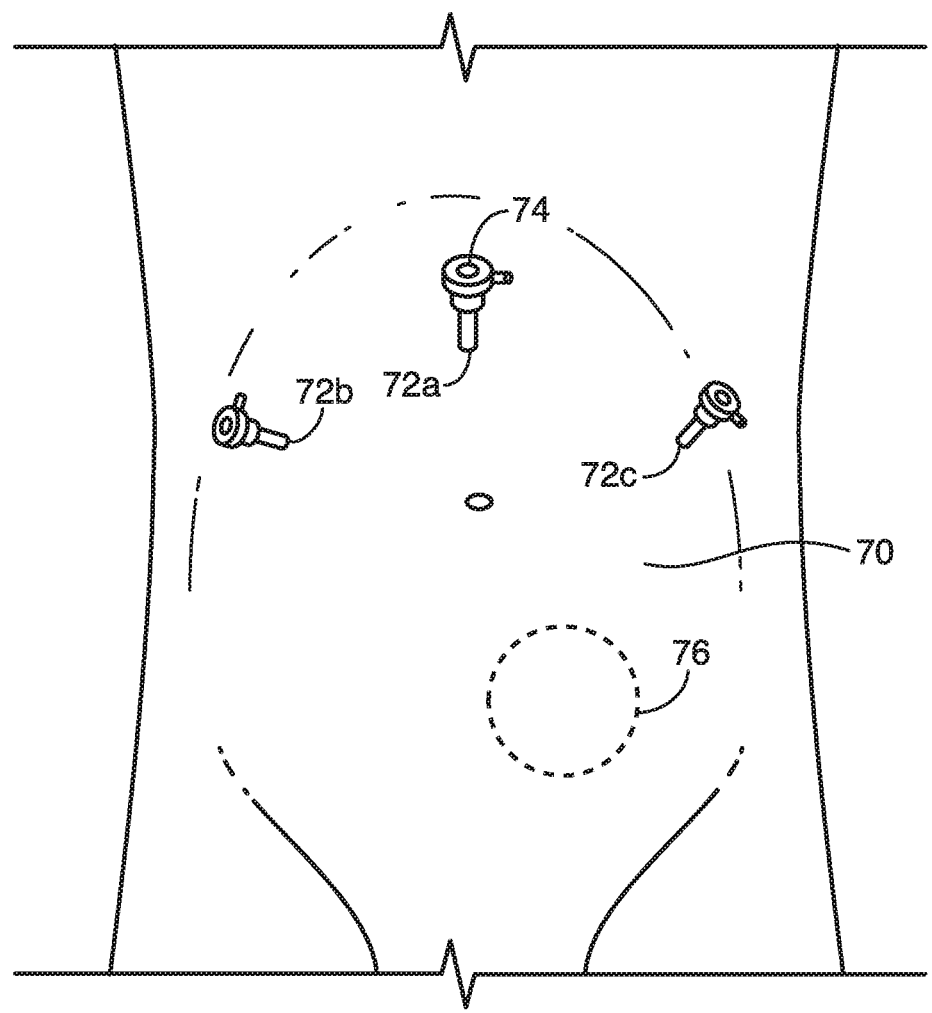
FIG. 14 is a front view of a patient showing one possible arrangement of ports on the abdomen for performing a laparoscopic surgical procedure.

Referring to FIG. 14, in general, a laparoscopic surgical procedure may involve making one or more small incisions (e.g., 5-15 mm) in the abdomen 70, thereby creating ports 72a-c through which a laparoscope, tools, or other instruments may be inserted. In certain embodiments, a cannula 74 may be used to hold the ports 72a-c open and to assist in inserting and removing objects or substances from the abdomen 70. A cannula 74 may come with a trocar (not shown) to pierce the abdomen 70 and thereby obtain access to a desired abdominal space.

For example, when treating a hernia 76, a camera port 72a may be positioned below the sternum to allow a clear view down the center of the abdomen 70. This also allows side ports 72b, 72c to be placed on either side of the abdomen 70 without blocking the view of the camera. One or both of the side ports 72b, 72c may be spaced laterally as far as necessary or possible to allow a surgeon to pass tools through the ports 72b, 72c to the abdominal wall to provide clear access to all parts of the patch 10. Additional ports may be added to access larger hernial defects as needed. The ability to inflate or otherwise swell and expand the patch 10 disclosed herein allows the patch 10 to be unfolded and positioned against the abdominal wall without the need for multiple instruments or sutures.

Figure 15:
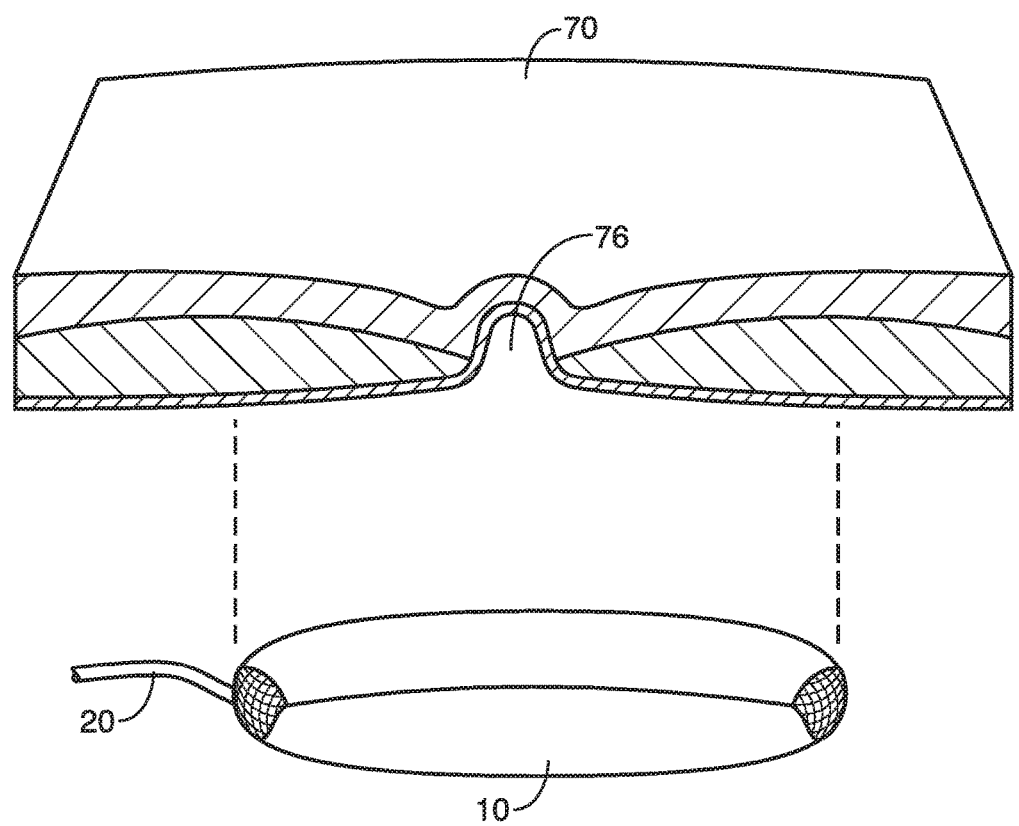
FIGS. 15 through 17 is a sectioned view of an abdomen showing a patch in accordance with the invention positioned to be used in a laparoscopic procedure.

Referring to FIG. 15, while continuing to refer generally to FIG. 14, in a laparoscopic procedure, a patch 10 may be rolled or folded and inserted through a port 72 in the abdomen 70. This may be accomplished, for example, by rolling the patch 10 around a sponge holder, forceps, or the like, and inserting the patch 10 through a port 72. If a conduit 20 is used to inflate or otherwise swell the chamber 18 to expand (e.g. lay out or extend) the patch 10, this conduit 20 may be routed through the port 72 to a fill mechanism such as a syringe, pneumatic bulb, a source of liquid or compressed gas, a pump, or the like outside of the abdomen. The patch 10 may then be positioned proximate the hernial defect 76.

Figure 16:
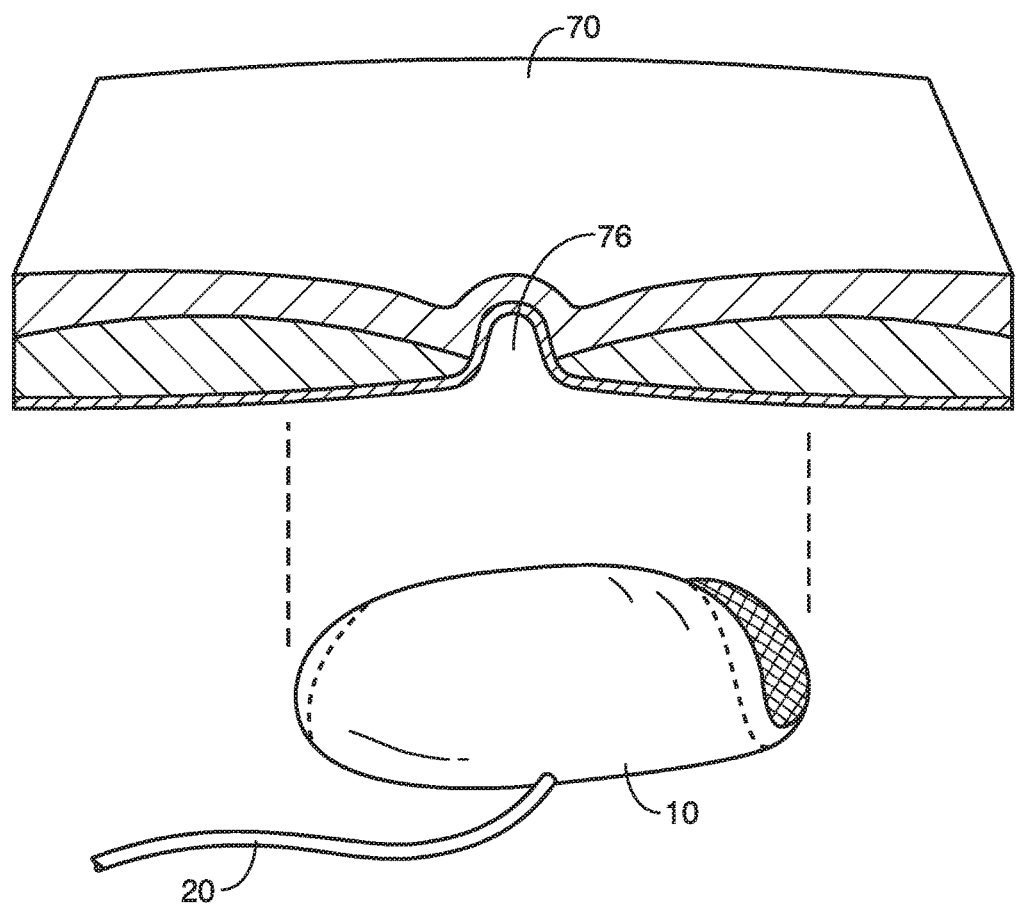

Referring to FIG. 16, once the patch 10 is positioned proximate the hernial defect 76, a fluid may be urged into the patch 10 through the conduit 20 to unfold, lay flat, and provide comparative stiffness to the patch 10.

Figure 17:
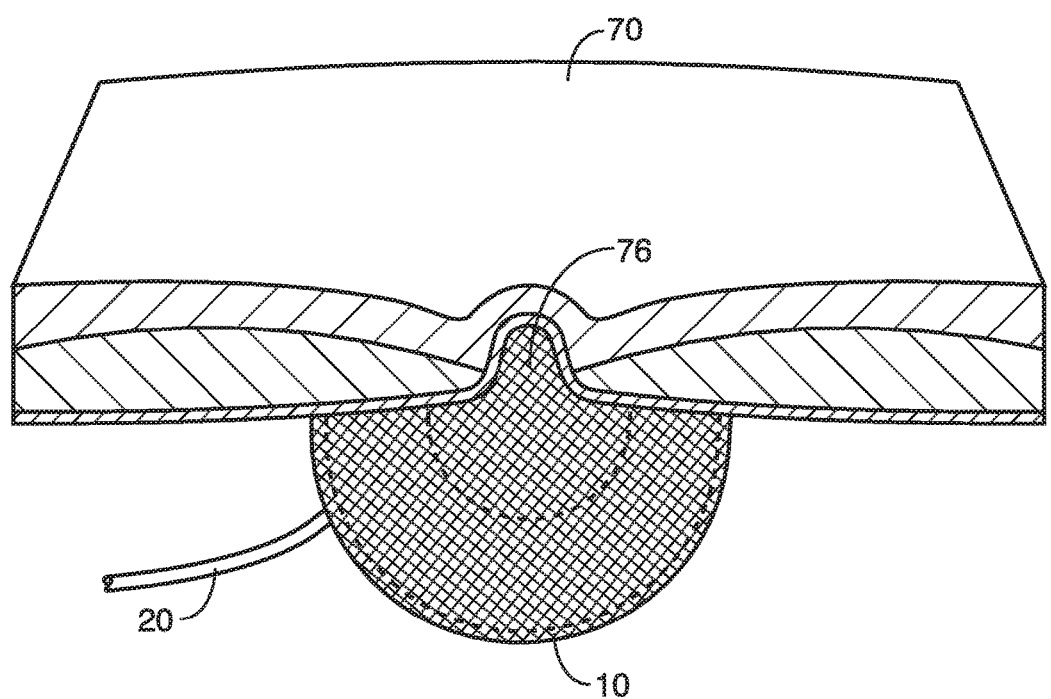

Referring to FIG. 17, once the patch 10 is inflated such that it lays substantially flat, the patch 10 may be positioned against the abdominal wall to cover the hernial defect 76. Ideally, the center of the patch 10 is positioned to be centered directly over the hernial defect 76 to allow adequate overlap beyond the outer edges of the defect 76. In selected embodiments, a suture may be passed through a small incision in the abdomen immediately above the hernial defect. This suture may be passed through the center of the mesh layer 12 of the patch 10. The suture may then be used to snug the patch 10 up against to the abdominal wall and center the patch 10 over the defect 76.

Once centered, the patch 10 may be attached to the abdominal wall with sutures, staples, or the like. This step may also puncture the fluid chamber 18, thereby allowing the patch 10 to deflate (e.g. drain or otherwise evacuate of gas or liquid). Alternatively, the patch 10 may be manually deflated by cutting the conduit 20, allowing fluid to escape through the conduit 20, allowing fluid to slowly leak through the chamber 18, or the like. After the chamber 18 is collapsed (e.g. emptied, deflated) and the conduit 20 removed, the incisions to the abdomen may be closed.

Figure 18:
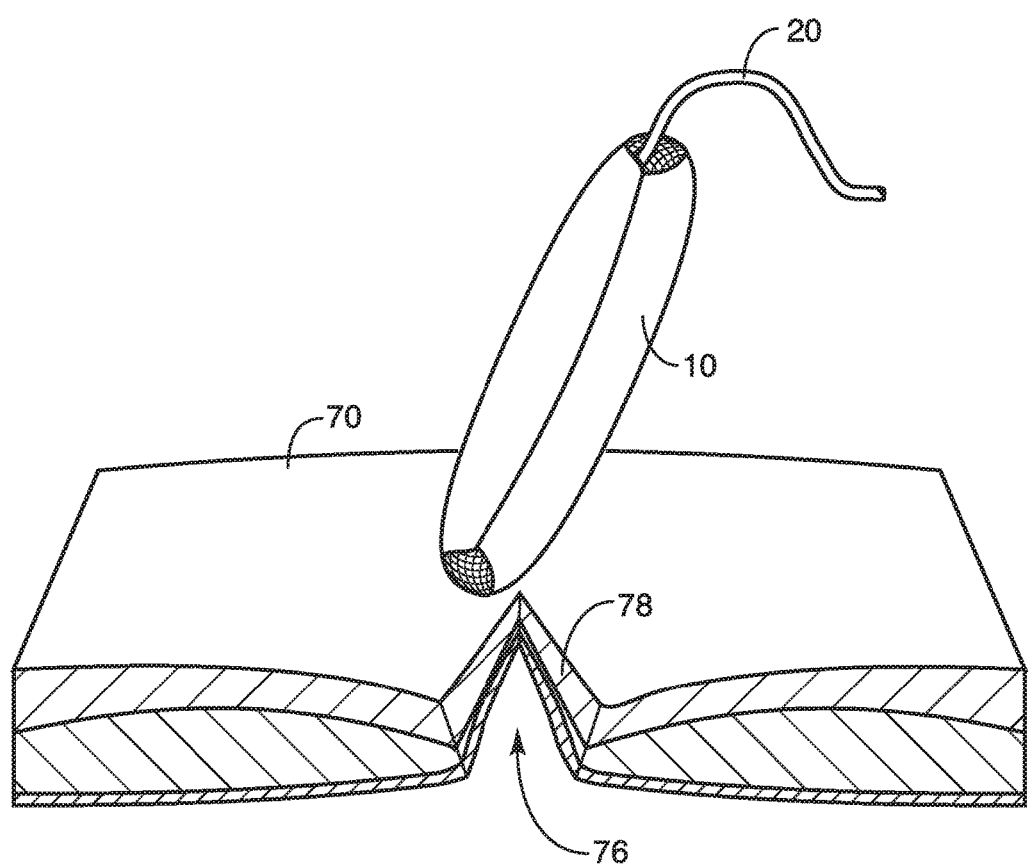
FIGS. 18 through 21 is a sectioned view of an abdomen showing a patch in accordance with the invention positioned to be used in an open surgical procedure.

Referring to FIG. 18, in an open surgery procedure, an incision 78 is typically made immediately over the hernial defect 76. The hernial sac may then be identified and opened, and the hernial sac's contents may be pushed back into the abdominal cavity. The surgeon may then clear out an intra-abdominal space (nominally a plane) around the defect perimeter in order to create an area and region for the patch 10 to rest against the abdominal wall.

Figure 19:
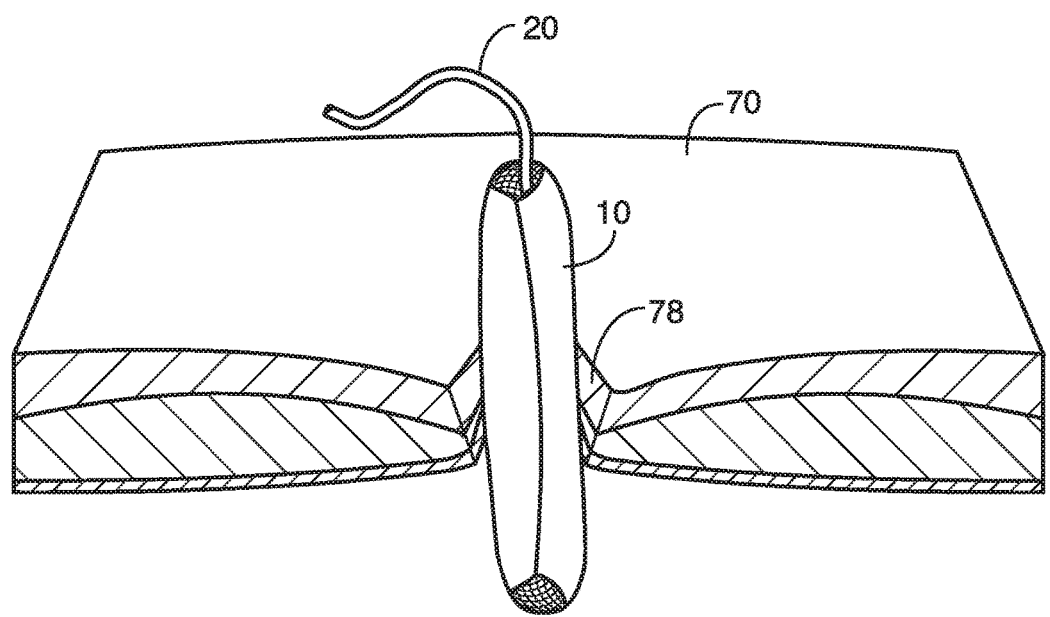

Referring to FIG. 19, once this region including a contact area for the patch is cleared, the patch 10 may be rolled or folded and inserted through the incision 78. As previously mentioned, this may include rolling or folding the patch 10 around a finger and then inserting the patch into the incision 78 with the finger. Alternatively, this may include simply compacting, such as by folding or rolling the patch 10, such as folding it into thirds, and inserting it through the open incision 78. Where used, a conduit 20 leading to the patch 10 may be routed through the incision 78.

Figure 20:
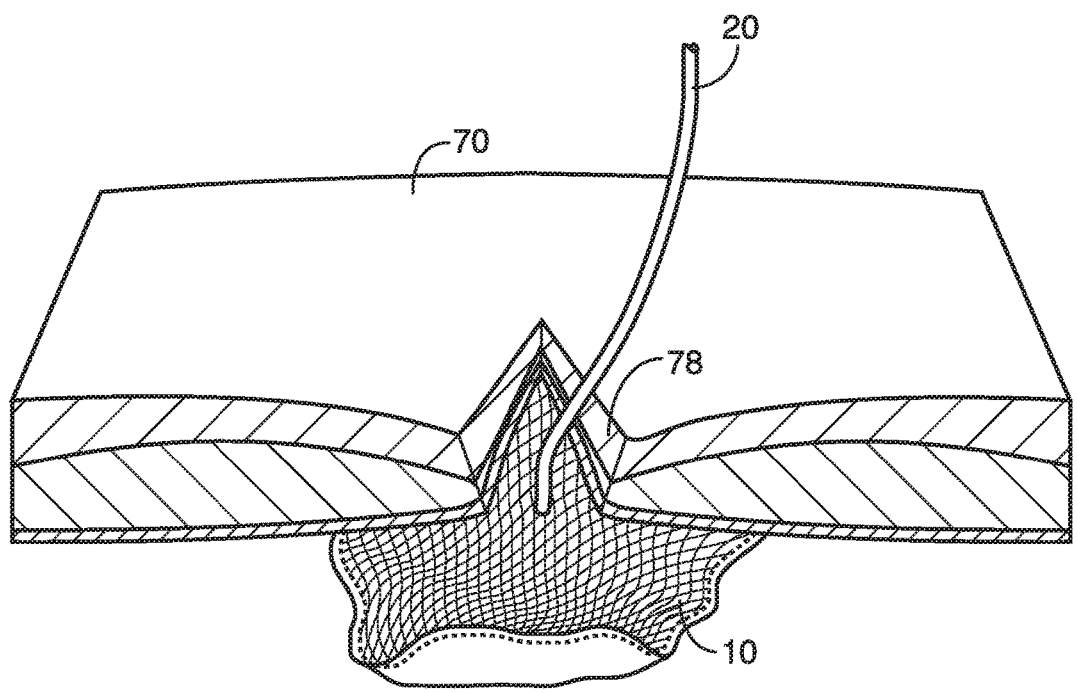

Referring to FIG. 20, once inserted and positioned about the hernial defect 76, a fluid may be urged into the patch 10 through the conduit 20 to unfold the patch 10 and provide rigidity (e.g. comparative stiffness) to the patch 10. As previously mentioned, the patch 10 may also be urged against the abdominal wall by gently pulling on the conduit 20 prior to attachment. This may also help the patch 10 to bend or flex to conform to the abdominal wall.

Figure 21:
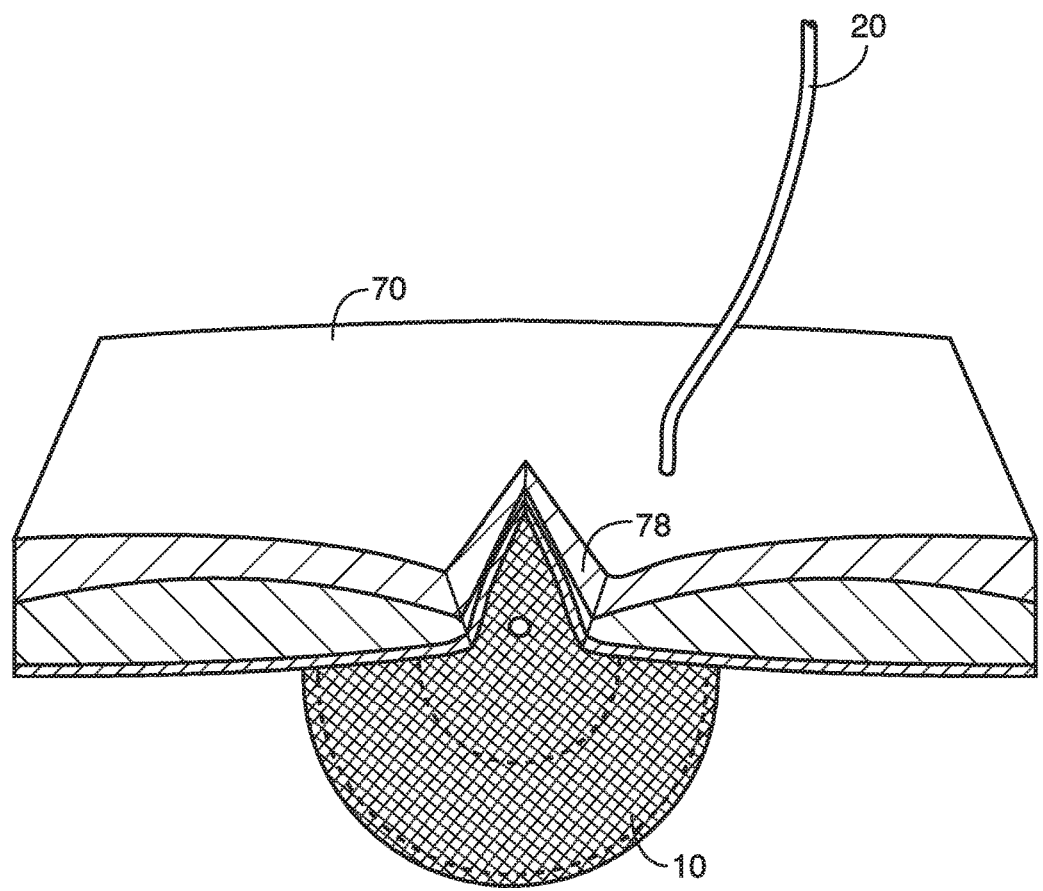

Referring to FIG. 21, once the patch 10 is inflated or otherwise filled to extend itself to an area where it can lie substantially flat, the patch 10 may be positioned against the abdominal wall about the hernial defect 76. As with previous examples, the center of the patch 10 is ideally positioned directly over the hernial defect 76 to provide adequate overlap beyond the outer edges of the defect 76. This may be accomplished by centering the conduit 20 through the incision. Once centered, the patch 10 may be attached to the abdominal wall with sutures, staples, or the like, which penetrators may also puncture the fluid chamber 18 to collapse the chamber 18 of the patch 10. Alternatively, the patch is deflated by cutting the conduit 20, allowing fluid to escape through the conduit 20, allowing fluid to slowly leak through the chamber 18, or the like. After the chamber 18 is collapsed and the conduit 20 removed, the incision 78 may be closed.

The present invention may be embodied in other specific forms without departing from its basic functions or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A medical implant for strengthening an intra-abdominal defect, the medical implant comprising:
    a mesh layer;
    a fluid chamber to contain pressure therethroughout;
    the fluid chamber forming at least one of a ring and a rib; and
    the fluid chamber connected to the mesh layer wherein inflation of the fluid chamber deploys the medical implant by extending the mesh layer toward a planar configuration.

2. The medical implant of claim 1, wherein the fluid chamber extends from one end of the medical implant to the other end of the medical implant when the medical implant is deployed.

3. The medical implant of claim 2, wherein the fluid chamber extends from one side of the medical implant to the other side of the medical implant when the medical implant is deployed.

4. The medical implant of claim 1, wherein the mesh layer comprises a plurality of interstices.

5. The medical implant of claim 4, wherein the fluid chamber further comprises a bioabsorbable, filler material extending to close the plurality of interstices.

6. The medical implant of claim 5, wherein:
    the mesh layer has a first perimeter; and
    the fluid chamber further comprises a containment layer having a second perimeter.

7. The medical implant of claim 6, wherein the first perimeter is fastened to the second perimeter to form an outer boundary of the fluid chamber when the medical implant is deployed.

8. The medical implant of claim 7, wherein the mesh layer is fastened to the containment layer at one or more locations inboard of the first and second perimeters.

9. The medical implant of claim 8, wherein containment layer comprises a bioabsorbable material.

10. The medical implant of claim 8, wherein the containment layer comprises an anti-adhesion layer formed of a polymer.

11. The medical implant of claim 10, wherein the polymer comprises a polyfluorinated material.

12. A medical implant for strengthening an intra-abdominal defect, the medical implant comprising:
    a mesh layer having a first perimeter;
    a fluid chamber extending proximate the first perimeter around a majority of the medical implant;
    the fluid chamber wherein pressure is containable therethroughout; and
    the fluid chamber connecting to the mesh layer toward a planar configuration; wherein the fluid chamber comprises: a second layer having a second perimeter; and a third layer having a third perimeter; wherein the second perimeter is fastened to the third perimeter to form an outer boundary of the fluid chamber when the medical implant is deployed; wherein the second layer is fastened to the third layer at one or more locations inboard of the second and third perimeters; wherein: the mesh layer comprises a plurality of interstices; and the second layer comprises a bioabsorbable, filler material extending to close the plurality of interstices wherein inflation of the fluid chamber deploys the medical implant by extending the mesh layer toward a planar configuration.

13. The medical implant of claim 12, wherein third layer comprises a bioabsorbable material.

14. The medical implant of claim 13, wherein the third layer comprises an anti-adhesion layer formed of a polymer.

* * * * *